United States Patent [19]
Hattler et al.

[11] Patent Number: 5,501,663
[45] Date of Patent: Mar. 26, 1996

[54] INFLATABLE PERCUTANEOUS OXYGENATOR WITH TRANSVERSE HOLLOW FIBERS

[75] Inventors: Brack G. Hattler; Harvey S. Borovetz, both of Pittsburgh, Pa.; Gary D. Reeder, Morrison, Colo.; Patricia J. Sawzik; Frank R. Walters, both of Pittsburgh, Pa.

[73] Assignee: Medtronic Electromedics, Inc., Parker, Colo.

[21] Appl. No.: 87,487

[22] Filed: Jul. 2, 1993

[51] Int. Cl.⁶ .................................................. A61M 37/00
[52] U.S. Cl. .............................. 604/26; 604/43; 604/96; 604/147; 128/DIG. 3; 261/DIG. 28; 422/45; 623/3
[58] Field of Search .................... 604/24–26, 43, 604/52, 53, 49, 96, 99, 101, 4, 147; 606/192, 194–196; 623/1, 3, 9, 11, 12; 128/DIG. 3; 261/DIG. 28; 422/45

[56] References Cited

U.S. PATENT DOCUMENTS

| | | | |
|---|---|---|---|
| 3,505,686 | 4/1970 | Bodell | 623/66 |
| 4,631,053 | 12/1986 | Taheri | 604/49 |
| 4,850,958 | 7/1989 | Berry et al. | 604/26 |
| 4,911,689 | 3/1990 | Hattler | 604/49 |
| 4,986,809 | 1/1991 | Hattler . | |
| 5,122,113 | 6/1992 | Hattler | 604/49 |
| 5,207,640 | 5/1993 | Hattler . | |
| 5,271,743 | 12/1993 | Hattler | 604/26 |

Primary Examiner—C. Fred Rosenbaum
Assistant Examiner—Ronald K. Stright, Jr.
Attorney, Agent, or Firm—Gary M. Polumbus; Holland & Hart

[57] ABSTRACT

An intravenous fiber membrane oxygenator is disclosed in several embodiments wherein the fibers either run at a transverse angle relative to the longitudinal axis of the oxygenator and/or are of a reduced length to optimize the gas transfer efficiency of the oxygenator. Various helical or spiral wraps of fibers are disclosed. One embodiment utilizes two sets of longitudinally extending fibers wherein the oxygen gas is moved in opposite directions from a central location of the oxygenator.

19 Claims, 11 Drawing Sheets

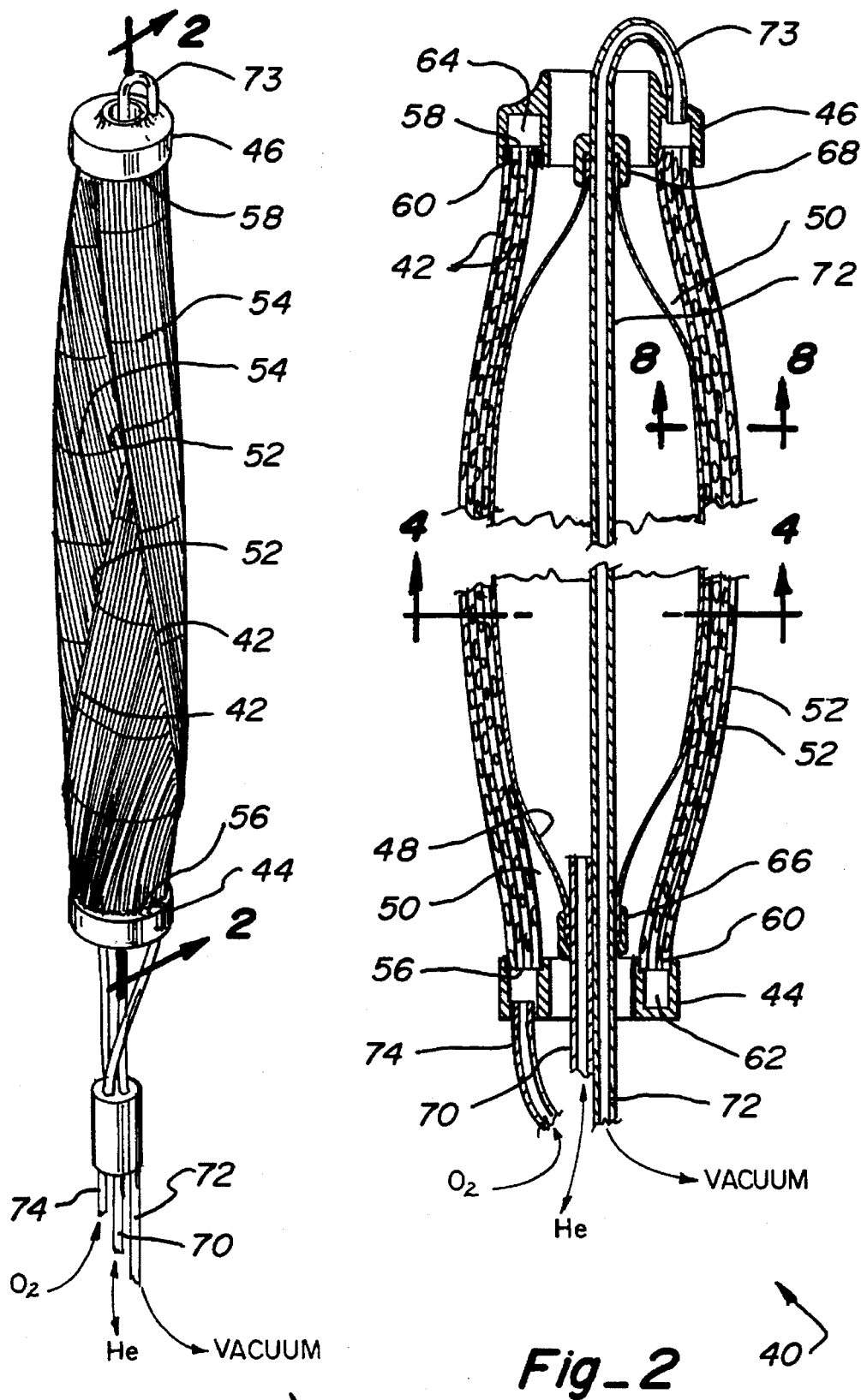

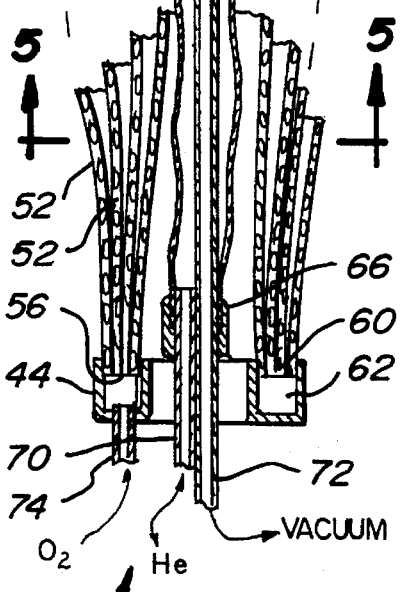
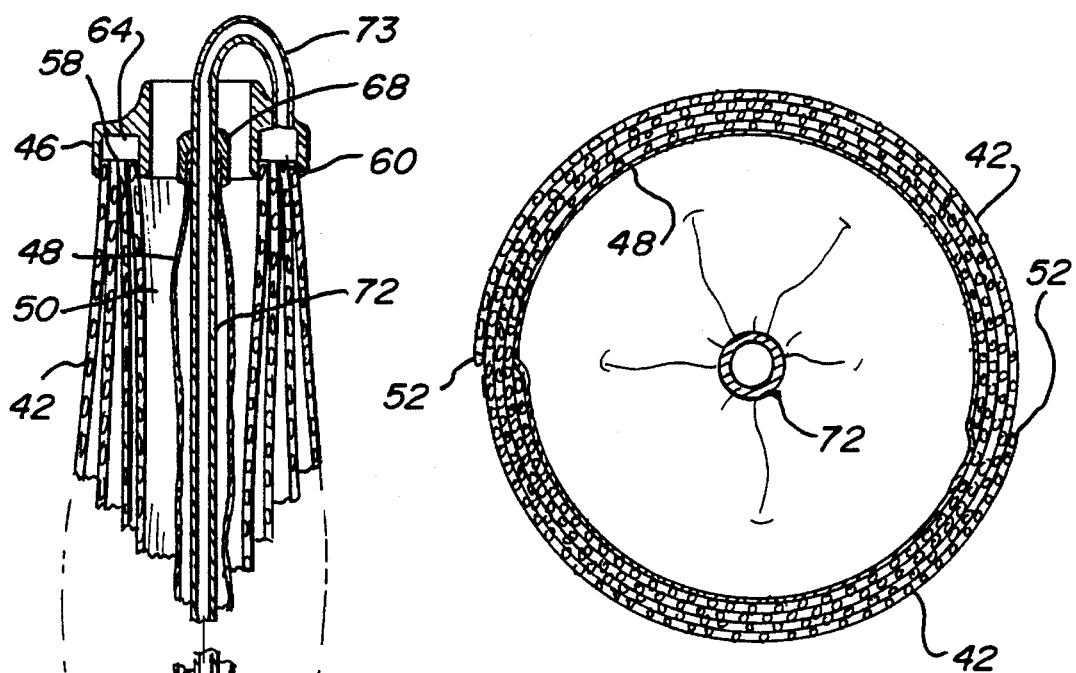
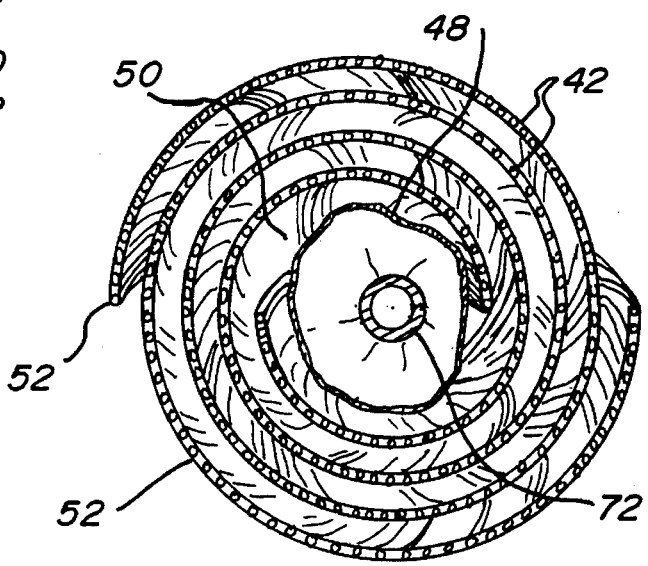
Fig_3
Fig_4
Fig_5

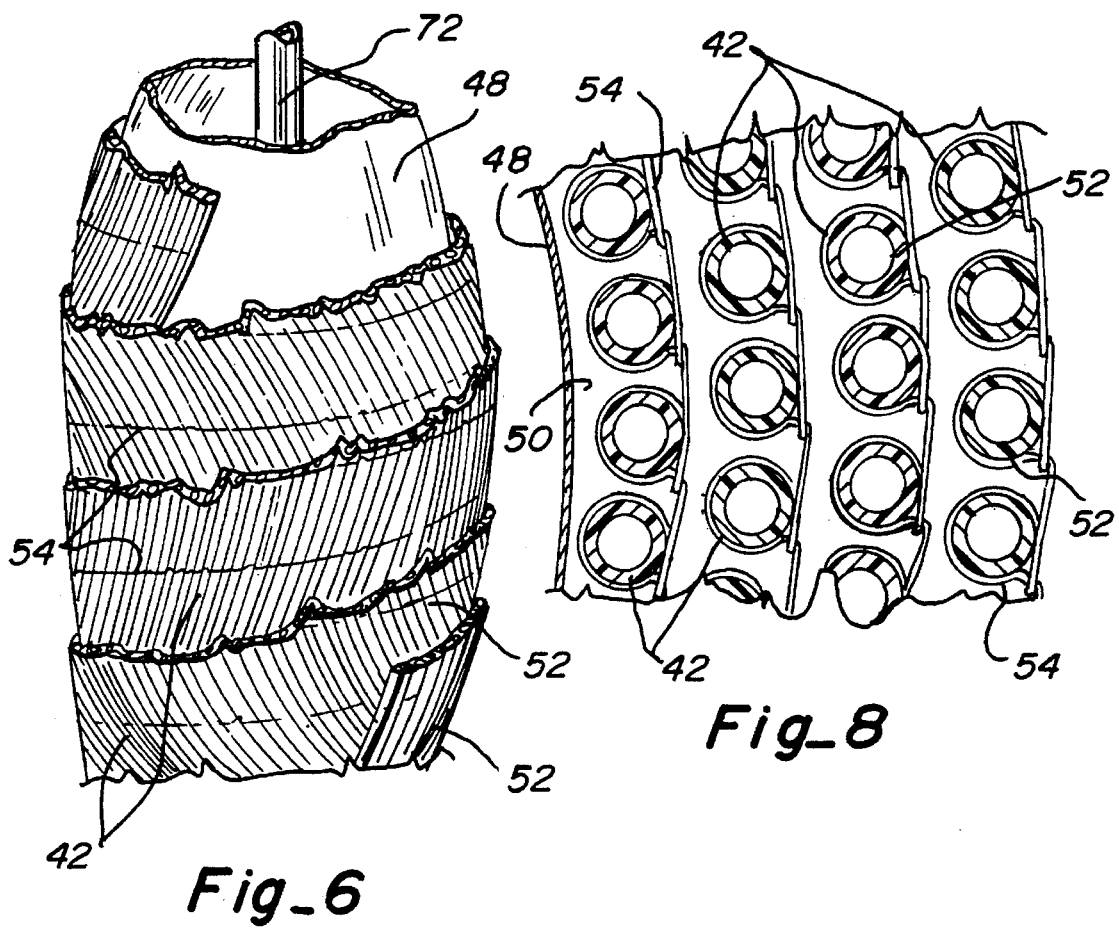
Fig_6  Fig_8
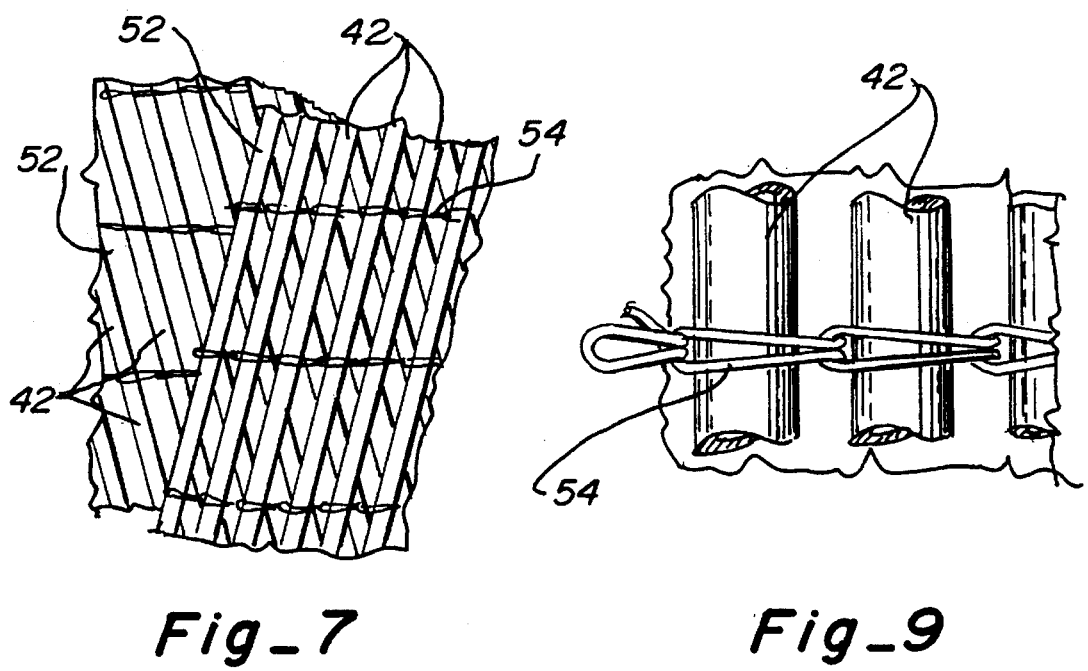
Fig_7  Fig_9

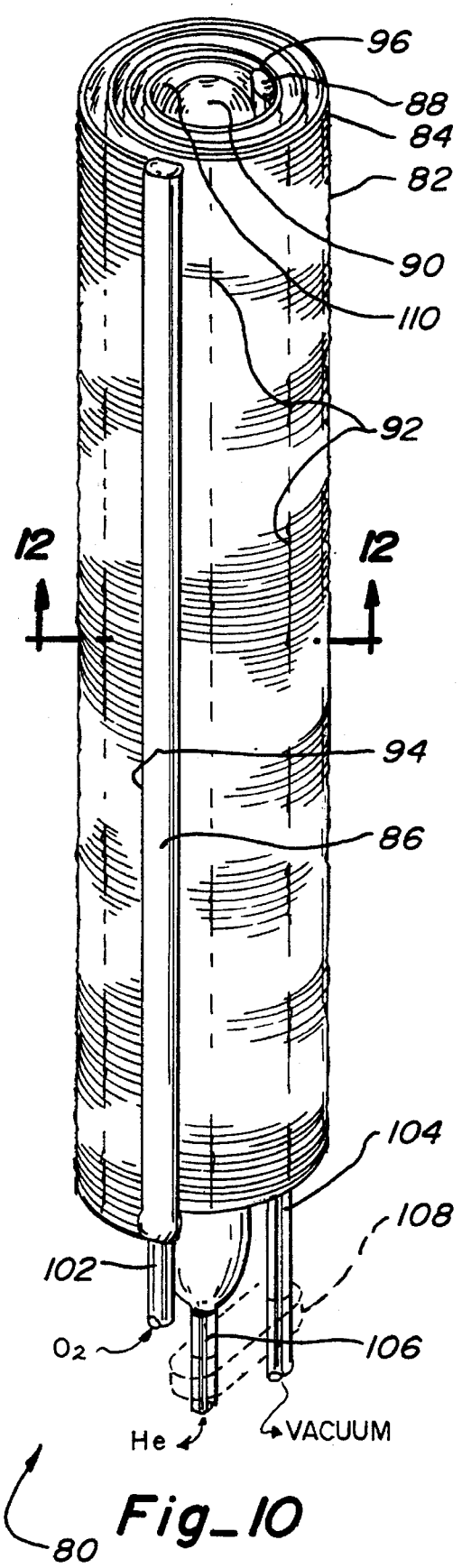
Fig_10
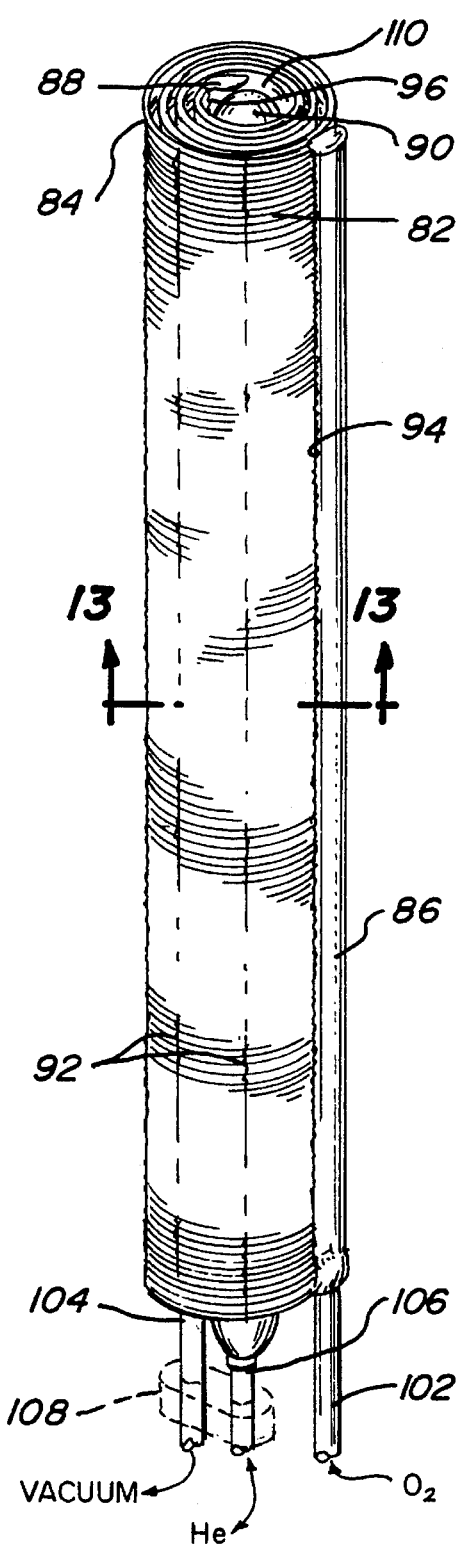
Fig_11

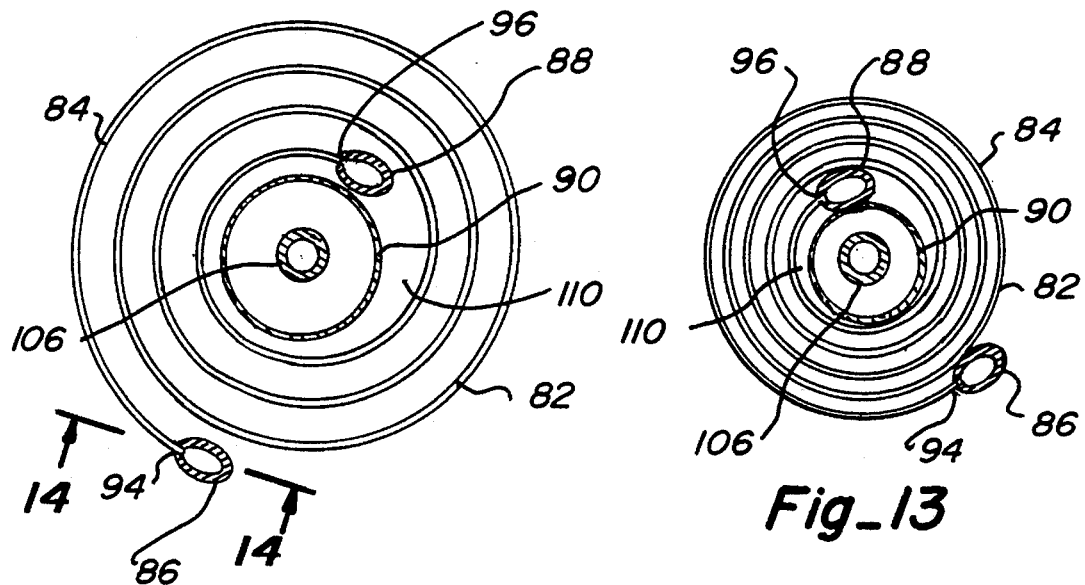
Fig_12   Fig_13
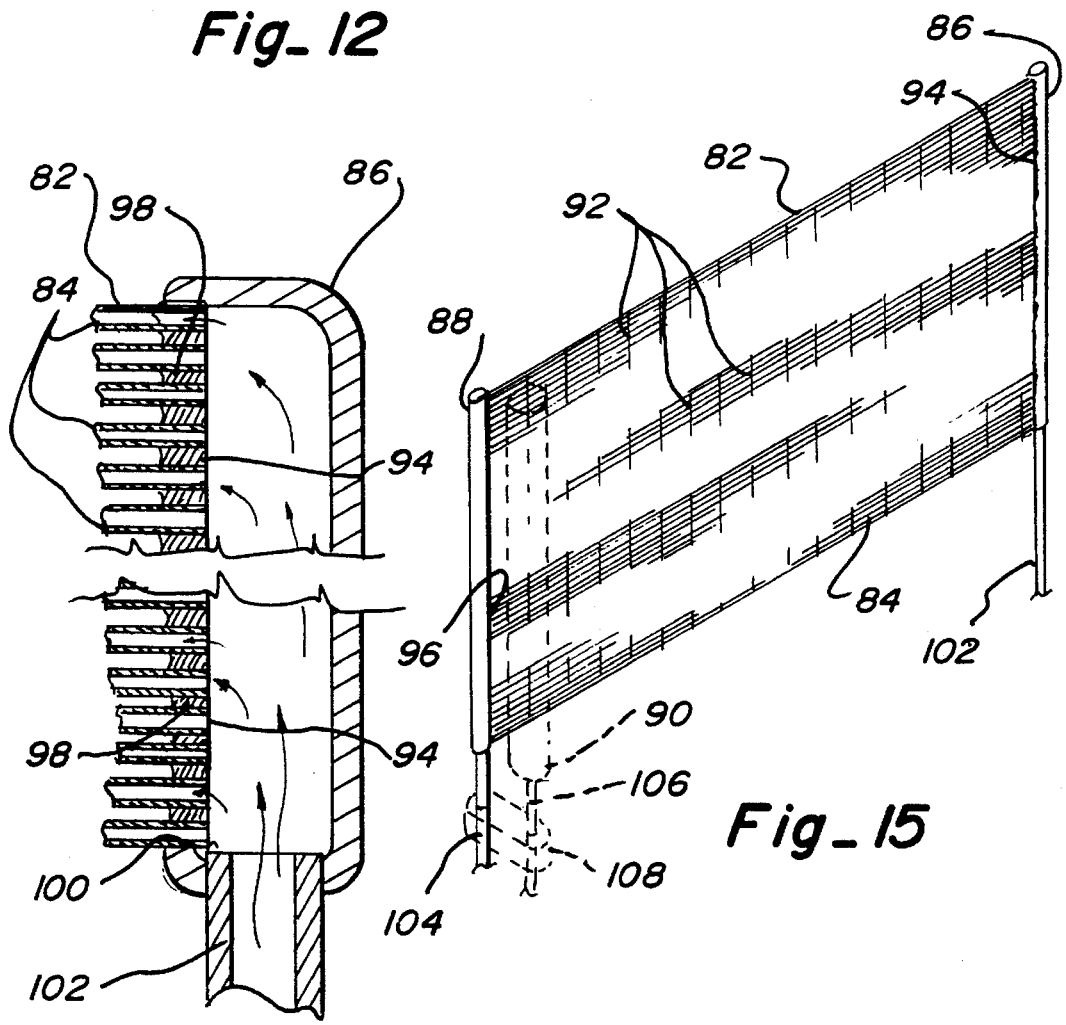
Fig_14   Fig_15

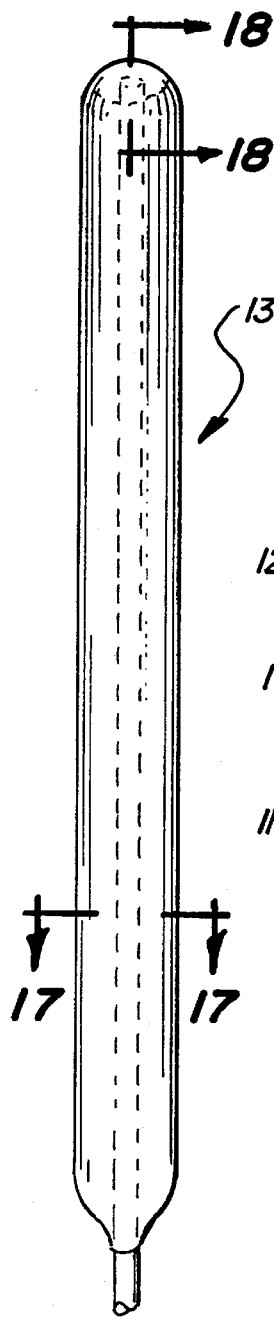
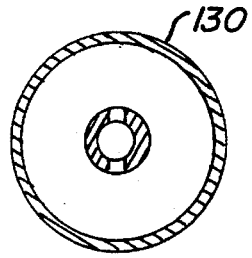
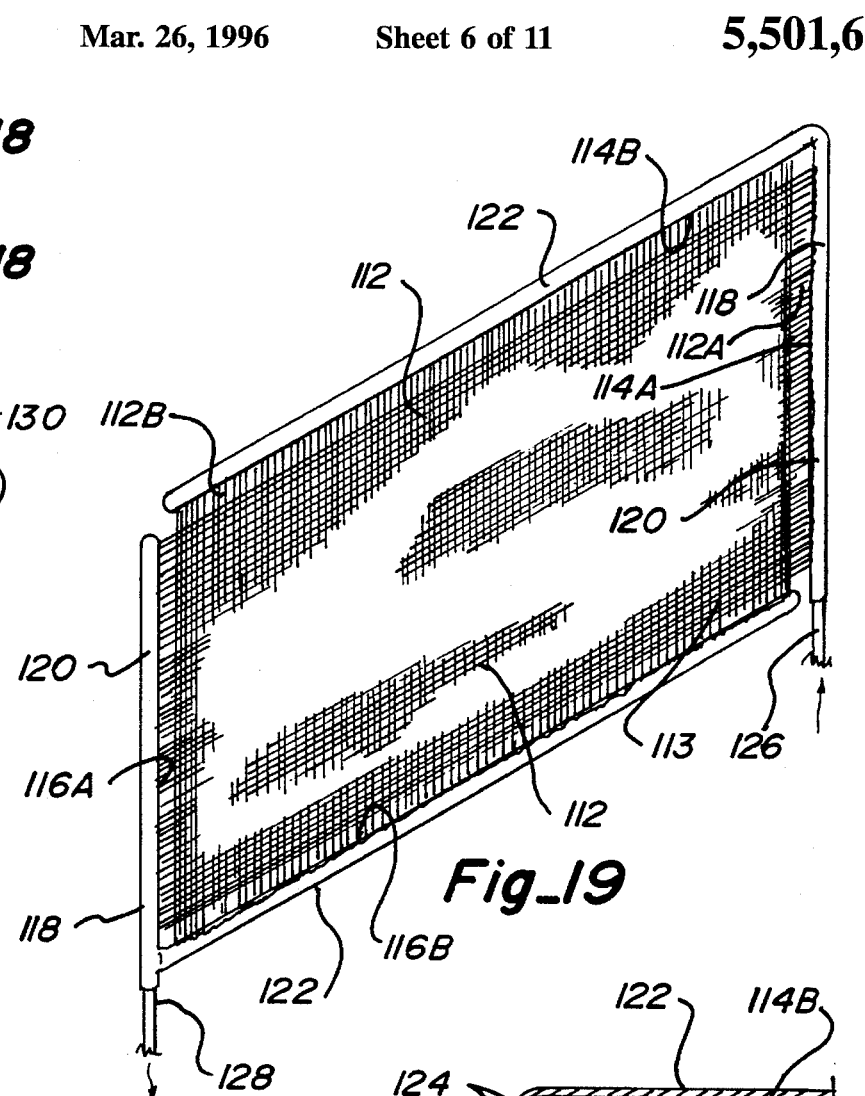
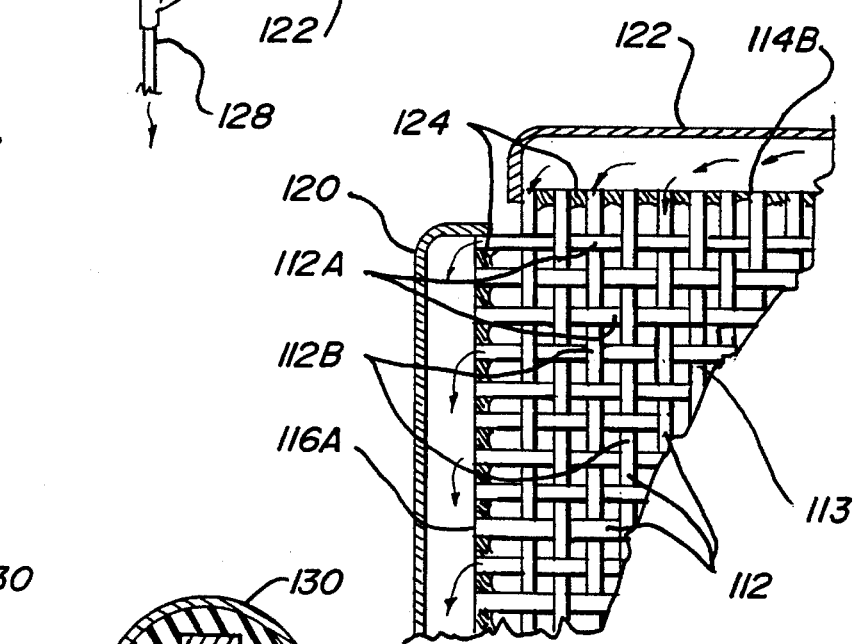

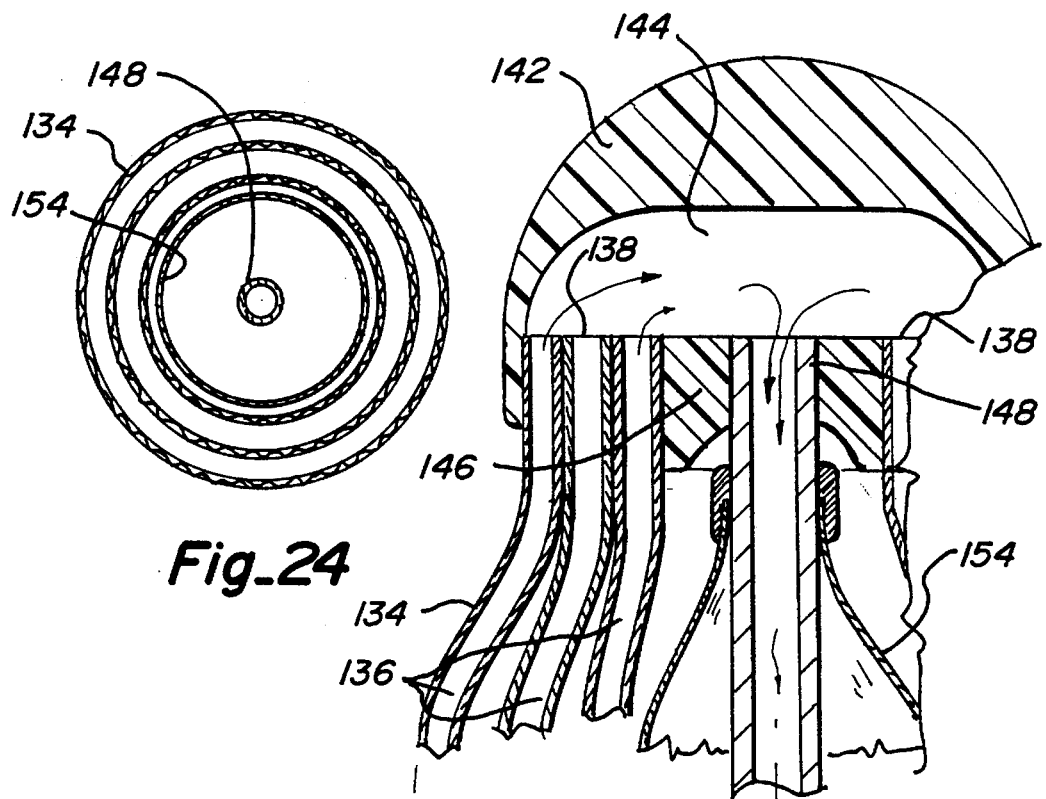
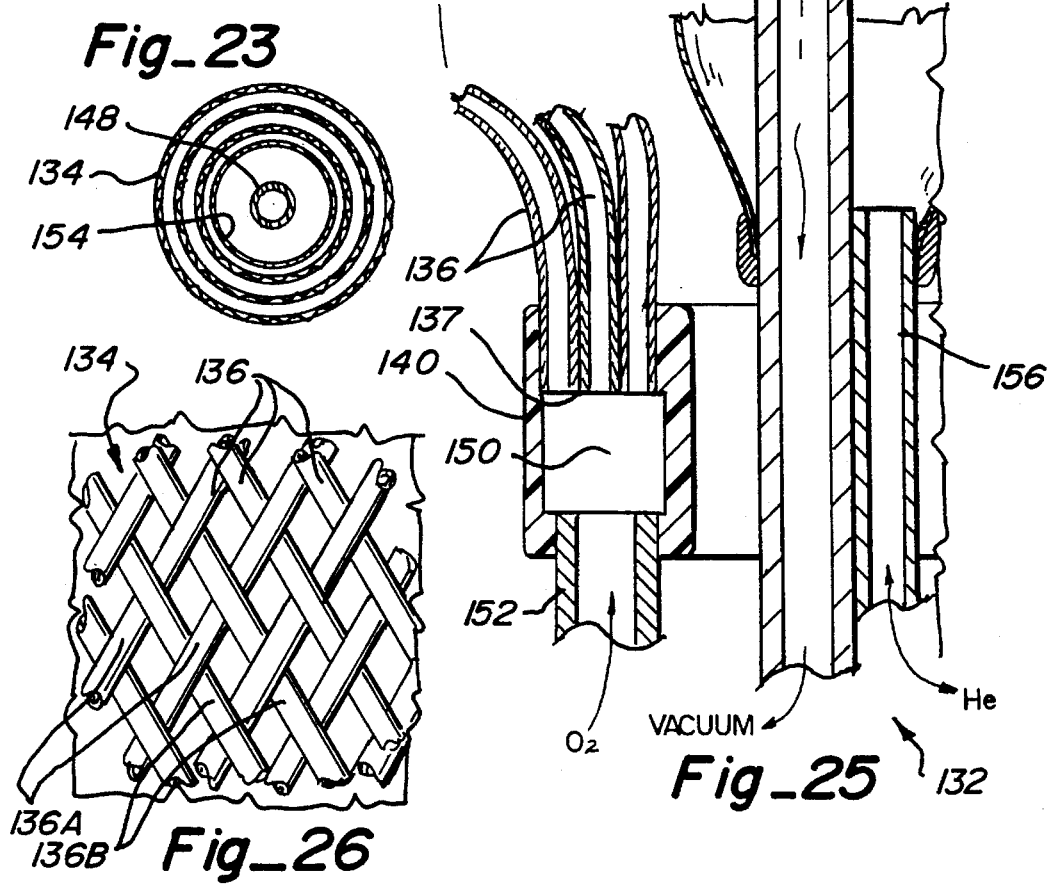

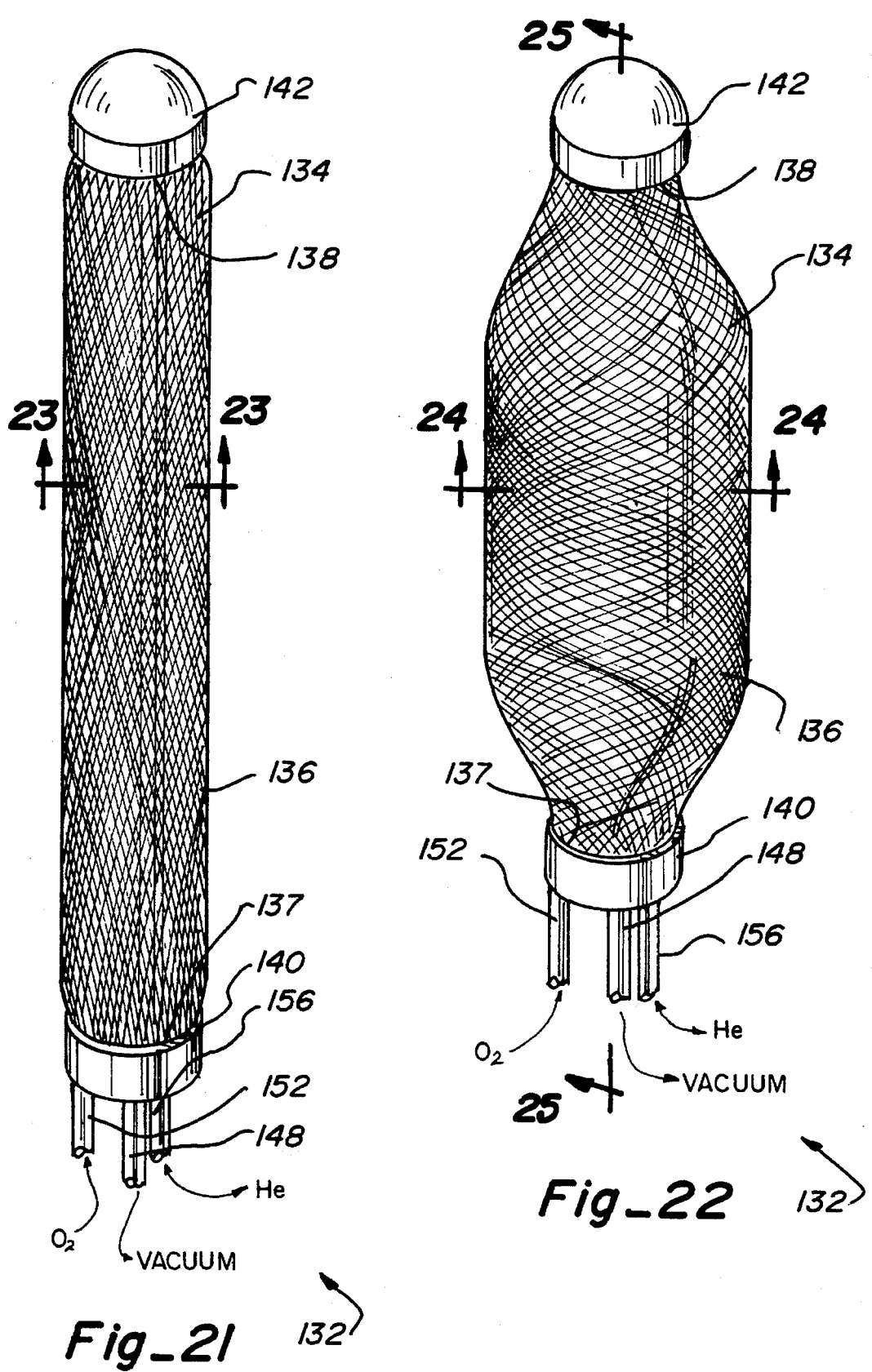

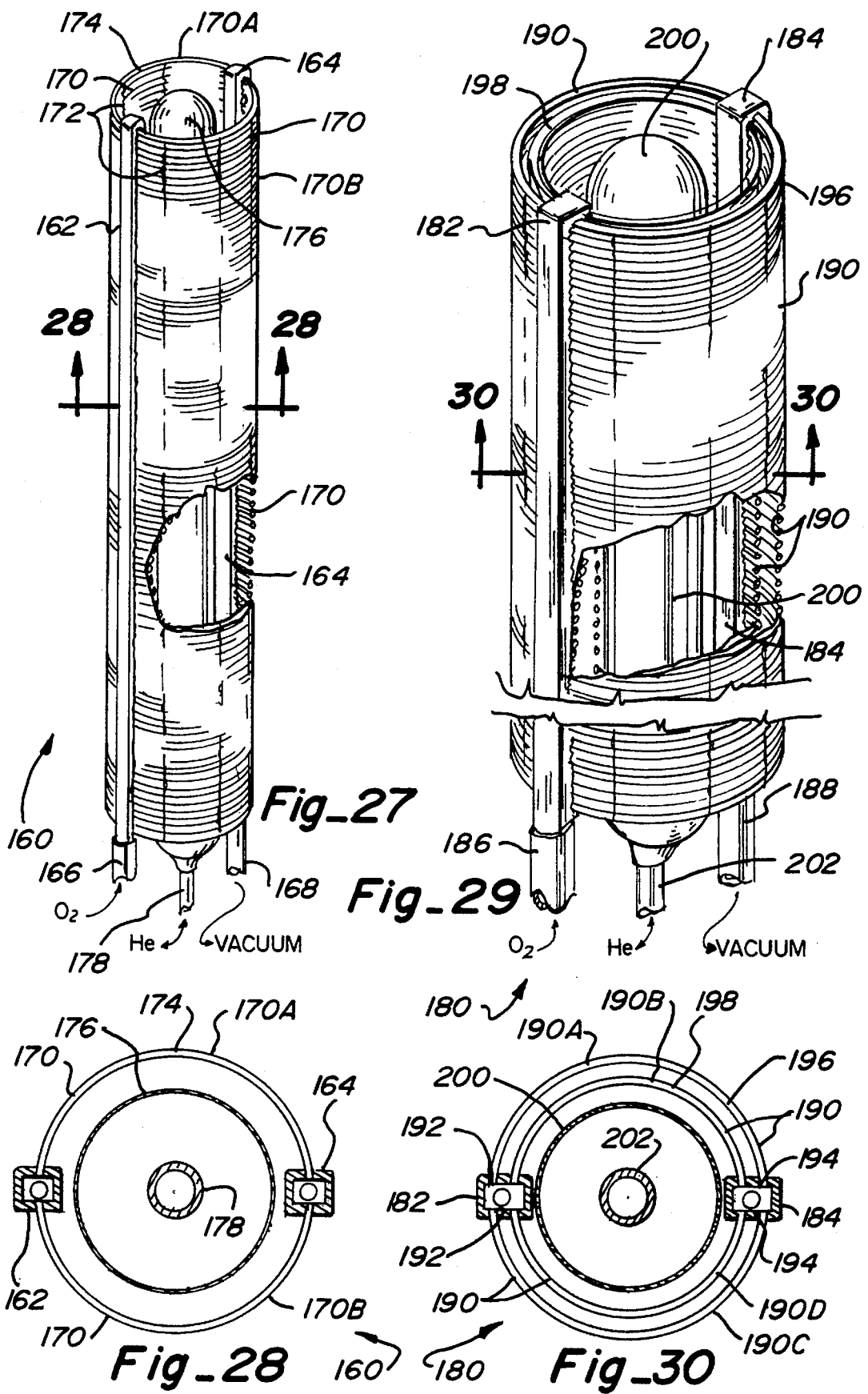

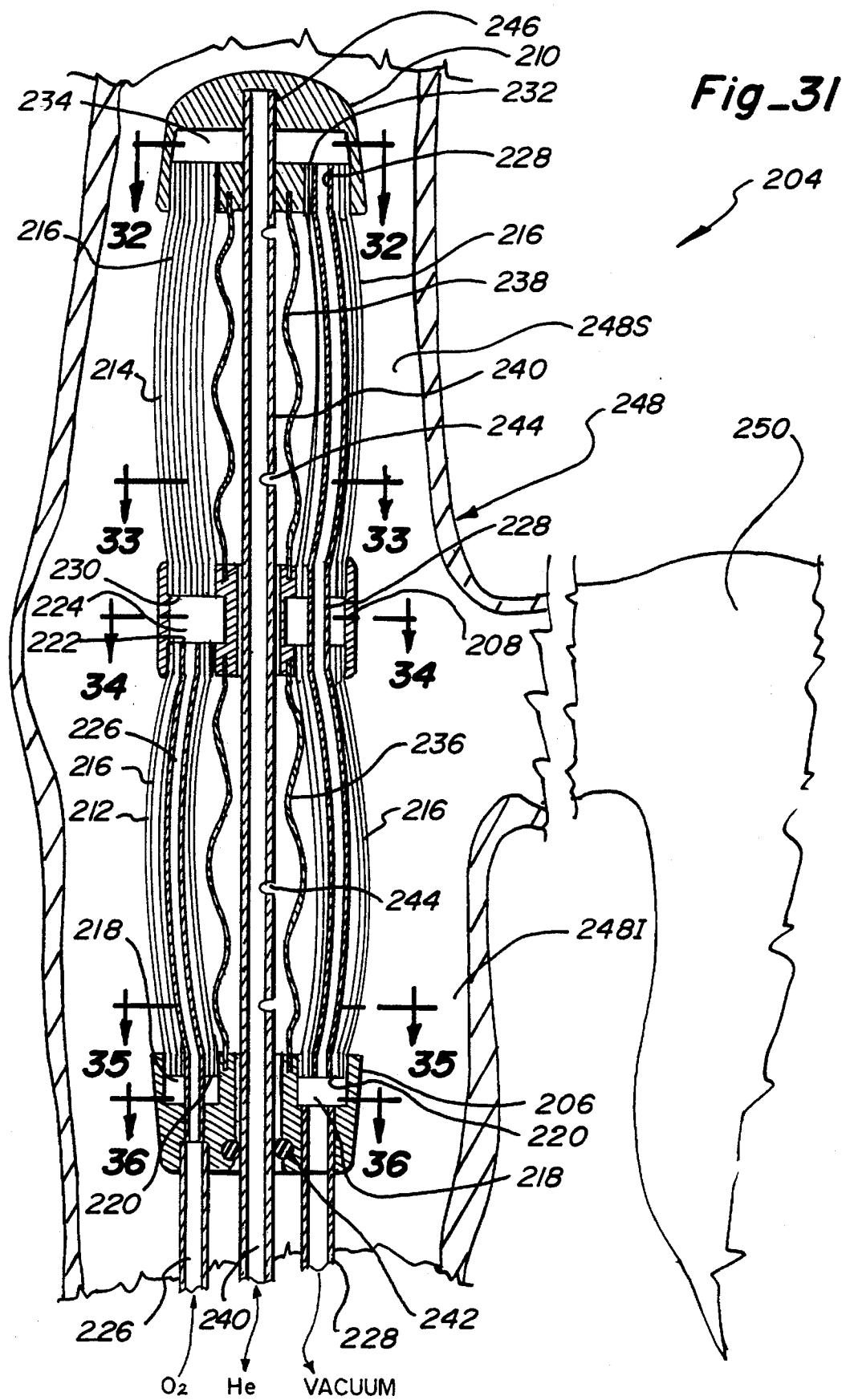
Fig_31

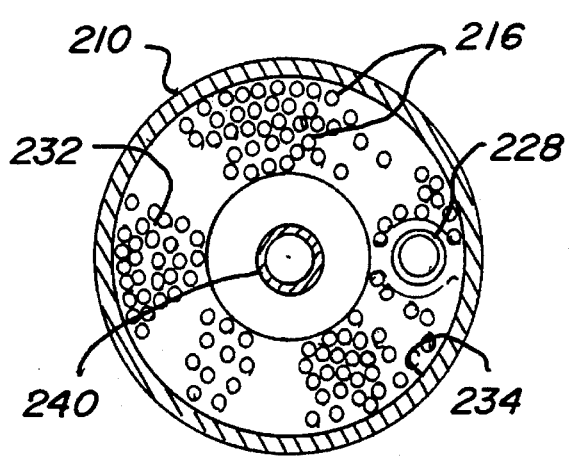
Fig_32
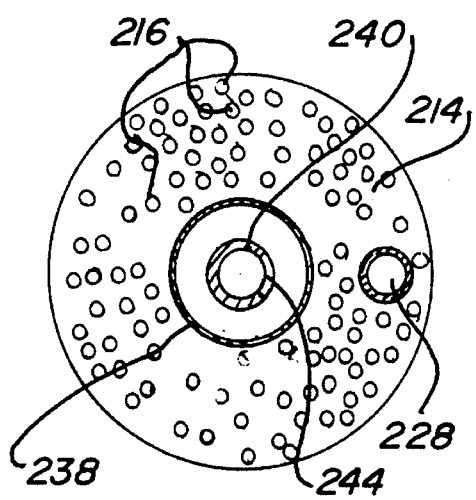
Fig_33
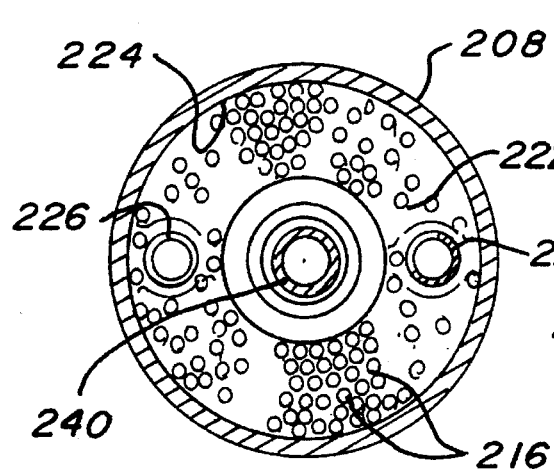
Fig_34
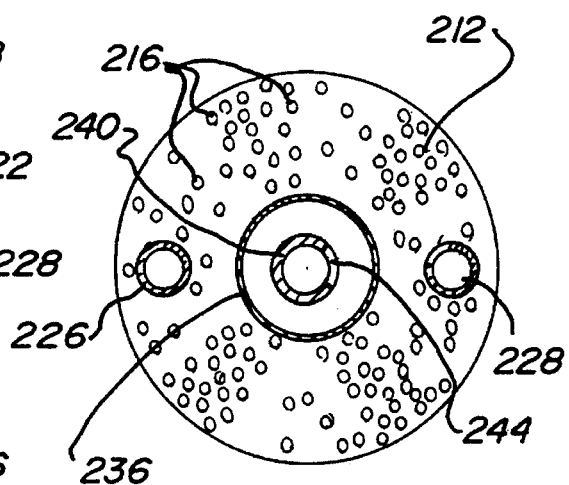
Fig_35
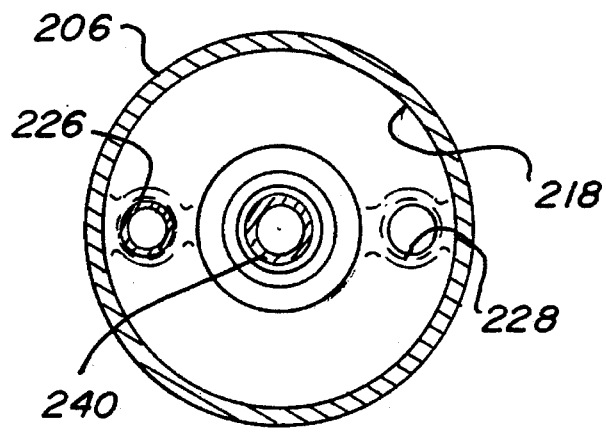
Fig_36

INFLATABLE PERCUTANEOUS OXYGENATOR WITH TRANSVERSE HOLLOW FIBERS

BACKGROUND OF THE INVENTION

1. Field of the Invention

The present invention relates generally to gas transfer devices and more particularly to a percutaneous intravenous oxygenator utilizing hollow gas permeable fibers.

2. Description of the Prior Art

Many types of blood oxygenators are well-known in the art. For example, during open heart surgery, the patient is interconnected with an external oxygenator, commonly known as a heart-lung machine, which introduces oxygen into the blood system. Most types of oxygenators use a gas permeable liquid impermeable membrane. Blood flows along one side of the membrane, and oxygen is supplied to the other side of the membrane. Given a sufficient pressure gradient between the oxygen supply and the blood, the oxygen will diffuse through the membrane and into the blood. In addition, carbon dioxide will tend to diffuse from the blood through the membrane. In other situations, a smaller, implantable oxygenator may be sufficient to adequately supplement the patient's cardiopulmonary function by marginally increasing the oxygen content of the patient's blood. For example, patients suffering from emphysema, pneumonia, congested heart failure, or other chronic lung disease often have blood oxygen partial pressures of approximately 40 torr. A relatively small increase of 10% to 20% is generally sufficient to adequately maintain the patient. This is a particularly desirable alternative in that it avoids the need to intubate the patient in such cases. In addition, temporary use of this type of oxygenator is sufficient in many cases to tie the patient over in acute respiratory insult. Placing such patients on a conventional respirator is often the beginning of a progressive down hill spiral by damaging the patient's pulmonary tree and thereby causing greater dependence on the respirator.

The effective rate of diffusion in percutaneous oxygenators can be limited in some instances by the problem of "streaming" or "channeling," in which the blood stream establishes relatively stable patterns of flow around and through the oxygenator. Portions of the oxygenator are exposed to a relatively high velocity, turbulent flow of blood. These conditions tend to increase cross-diffusion of oxygen and carbon dioxide. However, other portions of the oxygenator are exposed to a low velocity, laminar flow of blood which reduces diffusion of gases. Those portions of the oxygenator immediately adjacent to the regions of the high blood flow may continue to experience high rates of diffusion, but the remaining portions of the oxygenator tend to have relatively low diffusion rates. Thus, the overall diffusion rate of the oxygenator can be substantially diminished by streaming. A number of devices and processes have been invented in the past relating to different types of oxygenators.

U.S. Pat. No. 3,505,686 to Bodell demonstrates the general concept of using gas permeable fibers to boost the oxygen level of blood. The patent discloses several variations of the device wherein it is intended for use inside the body of the patient. In the implantable embodiment of the Bodell device, a tubular casing serves as a shunt either from the pulmonary artery to the left atrium of the heart or more generally between an artery and a vein. A multitude of parallel-connected capillary tubes are used to oxygenate and/or purify the blood circulating to the casing.

U.S. Pat. No. 4,583,969 to Mortenson shows a transvenous oxygenator made of a plurality of small diameter gas permeable tubes connected to headers at each end. However, the specific device disclosed by Mortenson has a significant disadvantage in that two incisions are required.

U.S. Pat. to Taheri No. 4,631,053 discloses a transvenous oxygenator having a single membrane through which oxygen diffuses. The membrane is disposed within a sheath and both are supported by a flexible wire.

U.S. Pat. No. 4,850,958 to Berry, et al. discloses an in vivo extrapulmonary blood gas exchange device having a bundle of elongated gas permeable tubes bound at each end and enclosed within respective air tight proximal and distal chambers. A dual lumen tube is situated relative to the gas permeable tubes such that an outer lumen terminates within the proximal chamber and inner lumen terminates within the distal chamber.

U.S. Pat. No. 4,911,689 to Hattler and U.S. Pat. No. 4,986,809 to Hattler, et al. disclose several embodiments of percutaneous oxygenators. In the simplest embodiment, oxygen is circulated through a plurality of hollow, gas permeable fibers forming loops and the device is inserted through a single incision into a blood vessel. In other embodiments, the fiber loops are bisected and placed in fluid communication within a mixing chamber within a tip at the distal end of the device.

Due to the inherent desirability and need for devices of the above-described type, continuing efforts are being made to improve the efficiency of the gas transferred provided by the device and it is to meet these needs that the present invention has been developed.

SUMMARY OF THE INVENTION

The present invention was developed to improve upon prior art oxygenators of the type that include hollow gas permeable/liquid impermeable membrane fibers that can be inserted into the vena cava to oxygenate blood intravenously. It has been found that the efficiency of such an oxygenators can be improved by minimizing the length of the fibers and/or deploying the fibers so that they do not run longitudinally of the device as in prior art systems. The blood gas transfer is also improved by maintaining constant movement of the gas fibers through use of an inflatable balloon around which the fibers extend.

Several embodiments of an oxygenator in accordance with the above teachings are disclosed with the first embodiment including several spirally wound sets of fibers each having input and output ends in communication with inlet and outlet manifolds. Each set of fibers is spirally wound in an opposite direction and surrounds an inflatable balloon which is connected to a gas inflation source for sequentially inflating and deflating the balloon to keep the fibers in constant motion. A gas delivery line is connected to the input manifold to deliver gas to the fibers and a vacuum source is attached to the output manifold so that the gas can be drawn through the fibers at a negative pressure.

In a second embodiment of the invention, an elongated tubular gas delivery manifold is connected to one end of a plurality of gas fibers with the manifold extending longitudinally of the oxygenator. A similar elongated tubular gas exhaust manifold is connected to the opposite end of the fibers and the fibers are wrapped around one of the manifolds as well as an inflatable and deflatable balloon so that several layers of the fibers can be wound transversely around the balloon. Circumferential displacement of the manifolds in one direction or another serve to increase or decrease the diameter of the oxygenator so that it can be decreased in diameter for easy insertion into the vena cava of a patient and increased in diameter while in the vena cava for optimal gas transfer.

In a third embodiment, two sets of gas permeable fibers are interwoven with the fibers of each set extending in parallel relationship with each other and substantially perpendicular to the fibers of the other set. One set of fibers extends longitudinally of the device and the other set transversely. An elongated semi-rigid manifold is connected in fluid communication to the input end of one set of fibers as well as to a substantially perpendicular but flexible elongated tubular manifold which is connected in communication to the input end of the fibers of the second set. A duplicate set of manifolds are connected to the outlet ends of the fibers so that the fibers and the flexible manifolds can be wound around one of the semi-rigid elongated manifolds and a balloon so as to be configured similarly to the second described embodiment. As will be appreciated, however, with this arrangement, twice the number of fibers can be utilized thereby increasing the gas transfer efficiency of the device.

A fourth embodiment of the invention includes two sets of fibers which have been woven and disposed about an inflatable balloon such that the fibers of each set wrap helically around the balloon. An inlet manifold and an outlet manifold are disposed at opposite ends of the device in communication with input and output ends of the fibers respectively so that gas can be delivered to the input ends of the fibers and removed by vacuum from the outlet ends. The balloon is again inflatable and deflatable to maintain the fibers in constant motion for optimal gas transfer. The manifolds are also longitudinally moveable relative to each other to allow the fibers to expand and contract in a desired manner.

In a fifth embodiment of the invention, elongated tubular inlet and outlet manifolds extend longitudinally of the device and are connected to inlet and outlet ends of gas permeable fibers which extend transversely to the manifolds and form a tubular construction of fibers around an interior inflatable balloon. Gas is delivered to the inlet manifold and allowed to flow in opposite directions through the fibers and around the tubular body for collection at the outlet manifold which is connected to a vacuum source so that the gas flow can be maintained at a negative pressure. Several layers of fibers comprising the tubular body can be provided in alternative arrangements of this embodiment.

In a final embodiment of the invention, at least three longitudinally spaced manifolds are provided with one of the manifolds being in communication with for example the input ends of two sets of fibers and the other two manifolds being in communication with the output end of both sets of fibers so that gas is transferred in opposite directions from an intermediate location on the device through both sets of fibers. The fibers surround inflatable balloons disposed between the manifolds at each end of the oxygenator and the middle manifold. A desirable feature of this embodiment is that the fibers are of relatively short length which has also been found to improve the gas delivery efficiency of the fiber membrane oxygenators.

Other aspects, features and details of the present invention can be more completely understood by reference to the following detailed description of the preferred embodiments, taken in conjunction with the drawings, and from the appended claims.

BRIEF DESCRIPTION OF THE DRAWINGS

FIG. 1 is an isometric view of a first embodiment of the present invention.

FIG. 2 is an enlarged fragmentary longitudinal section taken along line 2—2 of FIG. 1.

FIG. 3 is a longitudinal fragmentary sections similar to FIG. 2 with the balloon in a deflated condition.

FIG. 4 is an enlarged transverse section taken along line 4—4 of FIG. 2.

FIG. 5 is an enlarged fragmentary section taken along line 5—5 of FIG. 3 with parts removed to show the various layers of the oxygenator.

FIG. 6 is an enlarged fragmentary isometric with parts removed showing various layers of fibers.

FIG. 7 is a further enlarged fragmentary elevation showing the relationship of various layers of fibers.

FIG. 8 is an enlarged section taken along line 8—8 of FIG. 2.

FIG. 9 is an enlarged fragmentary elevation showing the interconnection of adjacent fibers in the oxygenator of FIG. 1.

FIG. 10 is an isometric view of a second embodiment of the present invention with an alternative arrangement shown in phantom lines.

FIG. 11 is an isometric view of the oxygenator shown in FIG. 10 in a reduced diameter configuration.

FIG. 12 is a section taken along line 12—12 of FIG. 10.

FIG. 13 is a section taken along line 13—13 of FIG. 11.

FIG. 14 is an enlarged fragmentary section taken through the inlet manifold of the oxygenator of FIG. 10 showing the connection of the manifold to the fibers.

FIG. 15 is an isometric view of the oxygenator of FIG. 10 in an unrolled state and with the balloon shown in phantom lines in the alternative arrangement.

FIG. 16 is an isometric view of a balloon used in a third embodiment of the present invention.

FIG. 17 is an enlarged section taken along line 17—17 of FIG. 16.

FIG. 18 is an enlarged section taken along line 18—18 of FIG. 16.

FIG. 19 is an isometric view of the third embodiment of the present invention in an unrolled state and without the internal balloon.

FIG. 20 is an enlarged section taken through portions of the inlet and outlet manifolds of the oxygenator of FIG. 19 showing their relationship with two interwoven sets of fibers.

FIG. 21 is an isometric view of a fourth embodiment of the present invention.

FIG. 22 is an isometric view of the embodiment shown in FIG. 21 in an expanded state.

FIG. 23 is an enlarged section taken along line 23—23 of FIG. 21.

FIG. 24 is an enlarged section taken along line 24—24 of FIG. 22.

FIG. 25 is a further enlarged longitudinal section with parts removed of the embodiment of the invention shown in FIG. 21.

FIG. 26 is a further enlarged fragmentary elevational view showing the woven relationship of the two sets of fibers utilized in the embodiment illustrated in FIG. 21.

FIG. 27 is an isometric view of a fifth embodiment of the present invention.

FIG. 28 is an enlarged section taken along line 28—28 of FIG. 27.

FIG. 29 is an isometric view with parts removed of a modification to the embodiment shown in FIG. 27.

FIG. 30 is a section taken along line 30—30 of FIG. 29.

FIG. 31 is a longitudinal section taken through a sixth embodiment of the present invention positioned within the vena cava and illustrating the heart adjacent thereto.

FIG. 32 is an enlarged section taken along line 32—32 of FIG. 31.

FIG. 33 is an enlarged section taken along line 33—33 of FIG. 31.

FIG. 34 is an enlarged section taken along line 34—34 of FIG. 31.

FIG. 35 is an enlarged section taken along line 35—35 of FIG. 31.

FIG. 36 is an enlarged section taken along line 36—36 of FIG. 31.

DESCRIPTION OF THE PREFERRED EMBODIMENTS

Referring first to FIGS. 1–9, a first embodiment 40 of the intravenous percutaneous oxygenator of the present invention can be seen to include a plurality of helically disposed hollow membrane fibers 42 having opposite ends in communication with ring like manifolds 44 and 46 and an internal inflatable balloon 48 disposed within a space 50 defined by the fibers. The fibers 42 are commercially available hollow membrane fibers which are gas permeable but liquid impermeable. A suitable fiber is manufactured by Mitsubishi and marketed under model no. KPF190M. The advantages of surrounding a balloon with the fibers resides in the fact that sequential inflation and deflation of the balloon will maintain the fibers in constant motion which improves the gas transfer or cross-diffusion of gas into and out of the fibers as is more clearly described in U.S. Pat. No. 5,122,113 which is hereby incorporated by reference.

Membrane type oxygenators are characterized in general by the fact that oxygen rich gas will diffuse through the membrane into oxygen deficient blood on the opposite side of the membrane while excess carbon dioxide in the blood will cross-diffuse through the same membrane into the oxygen stream. Accordingly, when a membrane oxygenator is inserted in a blood vessel and oxygen passed therethrough, the oxygen will diffuse through the wall of the fiber membrane thereby oxygenating the blood and simultaneously removing excess carbon dioxide from the blood.

It should be appreciated that the oxygenator of the present invention could be used in other gas transfer environments such as for example to deliver an anesthetic. A better description of this particular alternate use can be found in U.S. Pat. No. 5,207,640, which is hereby incorporated by reference.

The fibers 42 in the oxygenator 40 are actually deployed and helically wound in overlapping fiber mats 52 which consist of a plurality of substantially parallel fibers 42 that are transversely bound together as best shown in FIG. 9 by strands of thread 54 or the like which retain the fibers in a desired spaced relationship. Each fiber mat 52 includes a set of fibers having an input end 56 and an output end 58 with the input end of the fibers in each mat being embedded in a suitable potting compound 60 in the input manifold 44 so as to be in fluid communication with a ring-like chamber 62 in the manifold 44 at the proximal end of the oxygenator. The opposite or output ends 58 of the fibers in each mat are similarly potted in a suitable potting compound 60 in the output or exhaust manifold 46 so as to be in fluid communication with a ring-like chamber 64 in the exhaust manifold at the distal end of the oxygenator. The internal space 50 defined by the helically wound fiber mats 52 and the input and the output manifolds 46 and 48, respectively, functions to position and retain the balloon 48 which is fabricated from a tubular polymer sleeve wherein the ends of the tubular sleeve are hermetically sealed in rubber grommet 66 and 68 or the like. The grommet 66 at the proximal end of the balloon surrounds and hermetically confines a gas inflation tube or lumen 70 which communicates with the interior of the balloon and is connected to a source of helium or the like for inflating and deflating the balloon. The proximal grommet 66 also surrounds and hermetically confines a vacuum line or lumen 72 which extends through the balloon 48 as well as the grommet 68 at the distal end of the oxygenator before passing through a reverse loop 73 and being potted in the outlet manifold 46 in communication with the ring-like chamber 64 and the output ends of the fibers. The vacuum line 72 is connected at its proximal end to a source of vacuum (not shown).

The input manifold 46 has a gas inlet line or lumen 74 connected thereto which is exposed to a source of oxygen gas. The vacuum source connected to the vacuum line 72 serves to draw the oxygen gas into the oxygenator through the inlet manifold 46 where it is allowed to pass through the gas permeable fibers 42 while defusing into the blood. The gas mixture accumulating at the outlet manifold 46, which includes not only oxygen that did not diffuse but also carbon dioxide which cross diffused and was removed from the blood, is drawn from the oxygenator 40 through the vacuum line 72.

It is important to note that the balloon 48 is loosely disposed within the space 50 defined by the fibers so as to be slidable relative to the manifolds 46 and 48. Accordingly, when the balloon inflates, the manifolds can be drawn longitudinally toward each other and when the balloon is deflated, the manifolds can be longitudinally displaced from each other. This arrangement allows the fibers to move desirably for optimal gas transfer.

As is best illustrated in FIGS. 6 through 8, the fiber mats 52 on each layer of the oxygenator are helically wound with each layer being wound in an opposite direction. In one preferred embodiment of the oxygenator, each layer of fiber mat passes through approximately 180 degrees between its input and output ends. In other words, the input ends 56 of each fiber 42 are circumferentially offset approximately 180 degrees from the output ends 58.

A second embodiment 80 of the present invention is shown in FIGS. 10–15 and can be seen to include a fiber mat 82 formed of a plurality of parallel bound fibers 84 and elongated longitudinally extending tubular inlet and outlet manifolds 86 and 88, respectively, connected to opposite ends of the mat for delivering gas to the fibers and removing gas from the fibers. The entire mat 82 can be wound in a spiral around one of the manifolds and an interior balloon 90 which is inflatable and deflatable as with the first embodiment.

The fibers 84 in the fiber mat 82 extend substantially perpendicularly to the longitudinal axis of the oxygenator and are bound together as in the first described embodiment with threads 92 or the like so that the fibers are retained in substantially parallel but spaced relationship for optimal gas transfer. The inlet manifold 86 is connected to input ends 94 of each fiber 84 and the output manifold 88 is connected to the output ends 96 of each fiber as best seen in FIG. 14. The manifolds are semi-rigid tubes which retain the mat in a substantially extended condition while being flexible enough to be inserted into a vein and follow the contours of the vein. The manifolds 86 and 88 are hollow tubular bodies and the fibers are potted in a suitable potting compound 98 in an opening 100 in the side of the manifolds (FIG. 14).

It does not matter whether the inlet manifold 86 is disposed adjacent to the balloon 90 so that the fiber mat is wrapped therearound or whether the outlet manifold 88 is so positioned. For purposes of the present disclosure, however, the inlet manifold 86 is disposed on the outside of the oxygenator 80 and is connected via flexible tubing 102 to a source of oxygen (not shown). The outlet manifold 88 is similarly connected with flexible tubing 104 to a vacuum source (not shown) so that the vacuum source can draw the oxygen and any accumulated carbon dioxide through the manifolds and the connected fibers at a negative pressure.

The balloon 90 which is disposed interiorly of the wrapped fiber mat 82 is inflated and deflated in a conventional manner through a flexible tube 106 which is connected to a source of helium or the like which has been found to be suitable for this purpose. In an alternative arrangement of this embodiment, the balloon 90 might be connected to one of the manifolds 86 or 88 with a connector 108 which in the disclosed alternative shown in phantom lines in FIGS. 10, 11 and 15 is the outlet manifold 88. The connection of the balloon to one of the manifolds facilitates simultaneous insertion of the manifolds, mat and balloon. The connection does not necessarily have to be made, however, as the balloon can be inserted into the vena cava after the fiber mat is inserted and merely slid into the space 110 defined at the center of the spirally wound fiber mat.

A third embodiment of the invention is illustrated in FIG. 16–20 with this embodiment being somewhat similar to that disclosed in FIGS. 10–15. In the third embodiment, however, the fibers 112 are woven into a mat 113 so that there are two sets of parallel fibers 112A and 112B with the fibers in each set being substantially perpendicular to the fibers of the other set. Each set of fibers has an inlet end 114A or 114B and an opposite outlet end 116A or 116B. Manifolds 118 are generally L-shaped having a semi-rigid tubular manifold leg 120 and a perpendicular flexible tubular manifold leg 122. The rigid legs 120 are associated with one set of fibers 112A with one rigid leg communicating with the inlet ends 114A of the fibers and the other rigid leg with the outlet ends 116A of the fibers. Similarly, the flexible legs 122 are associated with the second set of fibers 112B with one flexible leg being in communication with the inlet ends 114B of the second set of fibers and the other flexible leg with the outlet ends 116B of the second set of fibers. The fibers 112 are suitably connected to the manifolds 118 with a potting compound 124 as shown in FIG. 20. One L-shaped manifold is of course connected to a source of oxygen (not shown) through an input line 126 while the other L-shaped manifold is connected to a vacuum source (not shown) through an outlet line 128.

The woven fiber mat 113 is wound around a balloon 130 configured as shown in FIG. 16 with the semi-rigid manifold leg 120 of each manifold 118 extending longitudinally of the oxygenator and in parallel relationship with the balloon. The flexible legs 122 of the manifolds are allowed to be wound into a spiral at proximal and distal ends of the oxygenator respectively. The woven mat 113 of fibers is therefore wound in a spiral around the balloon and the diameter of the oxygenator can be varied by moving the semi-rigid manifolds 120 circumferentially relative to each other in one direction or another to facilitate insertion and desired operation of the oxygenator. Of course, the ability of the semi-rigid manifolds to move circumferentially relative to each other allows the fiber mat 113 to expand and contract when the balloon is inflated and deflated respectively. One desired aspect of this embodiment of the invention is the fact that nearly twice the number of fibers can be incorporated into the same mat to increase the surface area of contact between the fibers and the blood to be oxygenated.

A fourth embodiment 132 of the present invention is illustrated in FIGS. 21–25. This embodiment can be seen to include a mat 134 woven from two set of fibers 136A and 136B with the fibers 136 in each set being substantially perpendicular to the fibers in the other set and with the sets of fibers being helically wound in opposite directions around the oxygenator. The fibers in each set have their inlet and outlet ends 137 and 138, respectively, potted in inlet and outlet manifolds 140 and 142, respectively, located at opposite longitudinal ends of the oxygenator. The outlet manifold 142, as best seen in FIGS. 21, 22 and 25, is merely a hollow cap defining an internal chamber 144 which is in communication with the outlet ends 138 of the fibers of both sets which are secured therein with a suitable potting compound 146. A hollow exhaust tube 148 has its distal end also imbedded in the potting compound 146 so as to be in communication with the chamber 144 whereby gas flowing through the fibers 136 into the outlet manifold 142 can be removed from the outlet manifold through the exhaust tube 148. The inlet manifold 140, which is at the proximal end of the oxygenator, is of ring-like configuration having a circular internal chamber 150 in communication with the inlet ends 137 of the fibers of both sets which are potted in the manifold. An oxygen supply line 152 is also potted in the inlet manifold 140 to deliver oxygen from an oxygen source (not shown) to the inlet manifold.

A balloon 154 is formed from tubular polymer material by hermetically sealing opposite ends of the tubular polymer material to the exhaust tube 148 at spaced locations along the length of the exhaust tube. The balloon is also hermetically sealed around a gas inflation line 156 which slidably extends through the inlet manifold 140. A source of helium gas or the like (not shown) is connected to the inflation line 156 to inflate and deflate the balloon. It should be appreciated that none of the balloon 154, the exhaust tube 148, or the gas inflation line 156 is connected to the inlet manifold so that the manifold 140 is allowed to slide along the length of these components toward and away from the exhaust manifold 142 as the balloon inflates and deflates. This permits the fibers to be moved in and out to optimize gas transfer.

The fibers 136, as mentioned previously, include two sets of interwoven fibers 136A and 136B which are disposed at an angle relative to the longitudinal axis of the oxygenator so that each fiber in fact is wrapped helically relative to the longitudinal axis of the oxygenator. As will be appreciated, when the manifolds 140 and 142 are separated longitudinally, the fibers tend to be drawn closer to a central longitudinal axis of the oxygenator, whereas when the manifolds are moved longitudinally closer to each other the fibers become further separated from the central longitudinal axis. This increases the turbulence of the blood passing in and around the oxygenator to optimize gas transfer.

A fifth embodiment of the present invention is illustrated in FIGS. 27–30 with a first arrangement 160 shown in FIGS. 27 and 28. In this arrangement, longitudinally extending inlet and outlet manifolds 162 and 164, respectively, are of elongated semi-rigid tubular construction and are diametrically disposed on either side of the oxygenator. Of course the inlet manifold 162 is connected through an inlet tube 166 to a source of oxygen gas (not shown) while the outlet manifold 164 is connected through an outlet tube 168 to a vacuum source (not shown). The fibers 170 are disposed in two sets 170A and 170B with each set being of generally semi-cylindrical configuration and having a plurality of parallel fibers that have been bound together with thread 172 or the like so as to retain the fibers in a spaced relationship and wherein they extend substantially perpendicularly to each of the manifolds. The fibers of each set extend away from each manifold in an opposite direction so as to define a tubular body 174 that surrounds an inflatable balloon 176. The balloon as in other embodiments is connected to a source of gas (not shown) through a gas supply tube 178 for inflation and deflation with a suitable gas being helium. One advantage with an embodiment of this type is that the length of each fiber 170 is relatively short which has been found to increase oxygen transfer efficiency of the oxygenator as a whole.

In a second arrangement 180 shown in FIGS. 29 and 30, elongated tubular semi-rigid input and output manifolds 182 and 184, respectively, are again connected to sources of oxygen gas through an input line 186 and a vacuum source through an outlet line 188, respectively. In this arrangement, however, there are actually four sets of fibers 190 which have been bound together into four mats 190A, 190B, 190C and 190D having inlet and outlet ends 192 and 194, respectively, of the fibers in each mat connected in fluid communication with the inlet and outlet manifolds 182 and 184, respectively. The four sets of fibers define in combination two concentric tubular bodies 196 and 198 which surround an internal balloon 200 which again is connected to a gas inflation and deflation source such as helium through a gas supply tube 202. The only difference in this arrangement and that shown in FIGS. 27 and 28 is that there is a double layer of thickness of the fibers to increase the surface area of contact between the fibers and the blood flow.

A sixth embodiment 204 of the present invention is shown in FIGS. 31–36 and can be seen to include three longitudinally displaced manifolds 206, 208 and 210 which interconnect two distinct sets 212 and 214 of fibers 216. The manifolds 206 and 210 at the opposite ends of the oxygenator serve a common purpose in serving as inlet or outlet manifolds while the middle manifold 208 serves the opposite purpose. For purposes of the present disclosure, the middle manifold will be referred to as the inlet manifold and the other manifolds 206 and 210 will be referred to as the proximal end outlet manifold and the distal end outlet manifold, respectively. The proximal end outlet manifold 206 of the oxygenator is ring shaped and defines an internal chamber 218 that is in communication with the outlet end 220 of the first set 212 of fibers which have been potted in the manifold. The inlet end 222 of the first set of fibers are potted in the inlet manifold 208 which also has a circular hollow chamber 224. An oxygen gas inlet line 226 is connected to (in non-fluid communication) and passes through the proximal end outlet manifold 206 and is connected to and communicates with the interior chamber 224 of the inlet manifold 208 for delivering gas to the inlet manifold. The gas is thereby allowed to flow in a reverse direction through the first set of fibers for collection in the proximal end outlet manifold 206 where the gas can be removed by a vacuum source connected through a vacuum line 228 to the hollow chamber 218 in the proximal end outlet manifold 206.

The second set of fibers 214 have their inlet end 230 potted in the inlet manifold 208 again in communication with the interior chamber 224 to receive oxygen gas therefrom and an outlet end 232 potted in the distal end outlet manifold 210 having a hollow chamber 234 in communication with the outlet end of the fibers. The vacuum line 228 extends through the proximal end outlet manifold 206, through the inlet manifold 208 (in non-fluid communication), and then opens into the internal chamber 234 in the distal end outlet manifold 210. In this manner, gas collected in the distal end outlet manifold can be returned to the proximal end outlet manifold 206 and subsequently removed from the oxygenator through the influence of the vacuum source.

It will therefore be seen that the inlet manifold 208 which is in communication with a source of oxygen gas is positioned to deliver gas to both the first and second sets 212 and 214 of fibers so that the gas flows in opposite directions from the inlet manifold and can be collected in both the distal and proximal end outlet manifolds for removal through the vacuum line 228. The vacuum source is therefore utilized to draw the oxygen gas through both sets of fibers at a negative pressure for optimal gas transfer with the blood.

A pair of inflatable balloons 236 and 238 are disposed interiorly of the two sets of fibers 212 and 214, respectively, with the balloons being made from a tubular stock of polymer wherein the open ends of the tubes are hermetically sealed at one end to the inlet manifold 208 and at the other end to the distal or proximal end outlet manifolds 210 and 206, respectfully. A semi-rigid tube 240 for delivering inflation gas to the balloons passes through the proximal end outlet manifold 206 and is hermetically but slidably sealed thereto by a rubber o-ring 242. The gas delivery tube has openings 244 along its length in communication with the interior of both balloons so that the balloons can be inflated and deflated by the injection and removal of helium gas or the like. The distal end 246 of the gas inflation tube is embedded and sealed in the distal end outlet manifold 210.

There are several advantages with this particular embodiment of the invention with one advantage being that while the oxygenator is of a length that is suitable for insertion into the vena cava, the gas delivery fibers themselves are of approximately half the overall length of the device. As mentioned previously, it has been found that better gas transfer can be obtained through shorter fibers carrying the same volume of gas. Another advantage with the oxygenator of this embodiment is that the oxygenator can be placed within the vena cava 248 in direct alignment with the heart 250 so that the oxygenator extends in opposite directions and actually delivers oxygen gas to the blood flowing from both the superior vena cava 248S and the inferior vena cava 248I into the heart 250. FIGS. 32–36 are cross-sectional views taken at different locations along the device as illustrated in FIG. 31 to better illustrate the relative positions of the component parts of the oxygenator.

It will be appreciated from the above description of the present invention that different embodiments of the oxygenator of the present invention have been illustrated which improve the gas transfer capabilities of intravenous fiber membrane oxygenators. Part of the improvement is felt to be due to the fact that the fibers extend at a transverse angle to the longitudinal axis of the oxygenator and also due to the fact that in several embodiments, the fibers have been shortened while retaining a desired surface area contact with the blood. Further, the embodiment of FIGS. 31–36 provides the advantage of delivering oxygen gas in two opposite directions so that the device is ideally suited for placement in direct alignment with the heart to oxygenate blood flowing from two opposite directions.

Although the present invention has been described with a certain degree of particularity, it is understood that the present disclosure has been made by way of example, and changes in detail of structure may be made without departing from the spirit of the invention, as defined in the appended claims.

We claim:

1. An elongated intravenous percutaneous oxygenator having a longitudinal axis comprising in combination:
    a balloon extending along the length of the oxygenator and a first lumen for delivering gas to said balloon and exhausting gas from said balloon, and
    a plurality of hollow gas permeable and liquid impermeable fibers surrounding said balloon, said fibers having an input end and an output end, a input lumen connected in fluid communication with the input end of said fibers, a output lumen connected in fluid communication with the output end of said fibers, gas moving means for delivering oxygen to said input lumen and removing gas from said output lumen, and gas inflation means in communication with said first lumen for inflating and deflating said balloon, at least some of said fibers extending to some degree transversely to said longitudinal axis said fibers being grouped in mats, there being a plurality of overlying layers of said mats.

2. The oxygenator of claim 1 further including a first manifold in fluid communication with the input end of said fibers, a second manifold in fluid communication with the output end of said fibers and wherein said fibers are spirally wound from their input end to their output end about the longitudinal axis of the oxygenator.

3. The oxygenator of claim 2 wherein there are several sets of said fibers with each set including a plurality of substantially parallel fibers and wherein the sets are at least partially overlapped and spirally wound in more than one direction.

4. The oxygenator of claim 3 wherein each set of fibers is spirally wound approximately 180° between said first and second manifolds.

5. The oxygenator of claim 4 wherein the fibers in each set are bound together in substantially spaced relationship to define said mats of said fibers.

6. The oxygenator of claim 3 wherein there is no fluid communication between said balloon and said first and second manifolds.

7. The oxygenator of claim 6 wherein said first and second manifolds are relatively movable along said longitudinal axis.

8. The oxygenator of claim 1 wherein there are first and second sets of fibers, said fibers of each set being substantially parallel with the fibers of the same set and being woven with the fibers of the other set and wherein the fibers of the first and second sets are spirally wound relative to the longitudinal axis of the oxygenator and around the balloon in opposite directions.

9. The oxygenator of claim 8 further including a first manifold in fluid communication with the input end of the fibers of both sets and said input lumen, a second manifold in communication with the outlet end of the fibers of both sets and said output lumen, and wherein said first and second manifolds are relatively movable along said longitudinal axis.

10. The oxygenator of claim 9 wherein output lumen extends through said balloon in hermetically sealed relationship therewith.

11. The oxygenator of claim 10 wherein said output lumen is slidably related to the manifold associated with said input lumen.

12. The oxygenator of claim 1 wherein the fibers of each mat are helically wound.

13. The oxygenator of claim 12 wherein the input end of each fiber is displaced approximately 180 degrees from the output end of the fiber.

14. The oxygenator of claim 13 wherein the fibers in each mat extend at an angle to the fibers in the next adjacent mat.

15. The oxygenator of claim 1 wherein said input and output lumens each include an elongated semi-rigid tubular manifold extending substantially parallel to said longitudinal axis and wherein said fibers extend substantially perpendicularly to said manifolds and in communication therewith, said fibers being oriented to form a hollow tube extending along said longitudinal axis in surrounding relationship with said balloon.

16. The oxygenator of claim 1 wherein said plurality of overlying layers of said mats are bound together in spaced relationship to form tubular mats of said fibers.

17. The oxygenator of claim 1 wherein there are first and second sets of said fibers, the fibers in each set extending substantially parallel to each other and substantially perpendicularly to the fibers in the other set, each of said input and output lumens including a semi-rigid and a flexible elongated tubular manifold, said manifolds of the input lumen being substantially mutually perpendicular and the manifolds of the output lumen being substantially mutually perpendicular, and wherein said fibers are wound around one of said semi-rigid manifolds and the balloon.

18. An elongated intravenous percutaneous oxygenator having a longitudinal axis comprising in combination:
    a balloon extending along the length of the oxygenator and a first lumen for delivering gas to said balloon and exhausting gas from said balloon, and
    a plurality of hollow gas permeable and liquid impermeable fibers surrounding said balloon, said fibers having an input end and an output end, a input lumen connected in fluid communication with the input end of said fibers, a output lumen connected in fluid communication with the output end of said fibers, gas moving means for delivering oxygen to said input lumen and removing gas from said output lumen, and gas inflation means in communication with said first lumen for inflating and deflating said balloon, at least some of said fibers extending to some degree transversely to said longitudinal axis,
    wherein said input and output lumens include elongated semi-rigid manifolds extending in parallel relationship with the longitudinal axis of the oxygenator and said fibers extend substantially perpendicularly to said manifolds, and wherein said fibers are wound around one of said manifolds and said balloon.

19. The oxygenator of claim 18 wherein said fibers are bound together in substantially parallel spaced relationship to form a mat of said fibers.

* * * * *